United States Patent [19]

Fujikura et al.

[11] Patent Number: 4,839,340
[45] Date of Patent: Jun. 13, 1989

[54] BORNANE-3-SPIRO-1'-CYCLOPENTANE DERIVATIVES AND PERFUMERY COMPOSITIONS CONTAINING THEM

[75] Inventors: Yoshiaki Fujikura; Tomohito Kitsuki, both of Utsunomiya; Manabu Fujita, Kashiwa; Nao Toi, Sakura, all of Japan

[73] Assignee: Kao Corporation, Tokyo, Japan

[21] Appl. No.: 213,151

[22] Filed: Jun. 29, 1988

[30] Foreign Application Priority Data

Jun. 29, 1987 [JP] Japan .................. 62-162137

[51] Int. Cl.$^4$ ................................ A61K 7/46
[52] U.S. Cl. ........................ 512/9; 568/665; 568/820; 560/256
[58] Field of Search ............ 568/665, 820; 560/256; 512/9

[56] References Cited

U.S. PATENT DOCUMENTS

| | | | |
|---|---|---|---|
| 3,681,464 | 8/1972 | Theimer | 568/665 |
| 3,860,638 | 1/1975 | Kitchens | 560/256 |
| 4,318,863 | 3/1982 | Sprecker et al. | 560/256 |
| 4,590,302 | 5/1986 | Scheidl et al. | 568/665 |
| 4,693,845 | 9/1987 | Fujikura et al. | 512/9 |

FOREIGN PATENT DOCUMENTS

| | | | |
|---|---|---|---|
| 55-108829 | 8/1980 | Japan | 512/9 |
| 60-19738 | 1/1985 | Japan | 568/820 |

*Primary Examiner*—James H. Reamer
*Attorney, Agent, or Firm*—Oblon, Fisher, Spivak, McClelland & Maier

[57] ABSTRACT

The invention provides derivatives of bornane-3-spiro-1'-cyclopentane with woody note scent useful as a base component in perfumery formulations which comprises those having a substituting group selected from a methoxyl, ethoxyl, formyloxyl and acetoxyl groups or two of substituting groups being either a hydroxyl group and a methyl group or a hydroxyl group and an ethyl group at the 2-position synthesized by any of the reactions of borane-3-spiro-1'-cyclopentan-2—ol or bornane-3-spiro-1'-cyclopentan-2-one with any of the reagents selected in accordance with the substituting group(s) to be introduced.

The invention also provides perfumery compositions containing the above.

8 Claims, No Drawings

BORNANE-3-SPIRO-1'-CYCLOPENTANE DERIVATIVES AND PERFUMERY COMPOSITIONS CONTAINING THEM

BACKGROUND OF THE INVENTION

The present invention relates to a novel derivative of bornane-3-spiro-1'-cyclopentane and a perfumery composition containing it.

In recent years, synthetic perfumes have been given much weight as the base material for perfumeries getting rid of dependence on the natural resources common in the prior art in order to satisfy various requirements such as stationary supply, invariability in the quality, inexpensiveness and the like.

Notwithstanding the above, natural perfumes are still given much weight concerning the woody not scent so that supply of synthetic substances with woody note scent is wished in consideration of the increase of demand in the future.

However, difficulties are posed in many of the cases of industrial production of the compounds with woody note scent since many of such compounds have a polycyclic structure with complexity as typically represented by sesquiterpenes. In particular, synthesis of tricyclic compounds was not easy among such polycyclic compounds.

SUMMARY OF THE INVENTION

The present invention is a compound with woody note scent useful as a basic component for formulating various types of perfumeries which is a derivative of bornane-3-spiro-1'-cyclopentane represented by the general formula

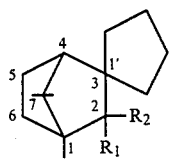

(I)

in which $R_1$ represents a hydrogen atom or a hydroxyl group and $R_2$ represents a methoxyl group, an ethoxyl group, a formyloxyl group or an acetoxyl group in the cases in which $R_1$ is a hydrogen atom or represents a methyl group or an ethyl group in the cases in which $R_1$ is a hydroxyl group.

The present invention also includes a perfumery composition containing the above derivative of bornane-3-spiro-1'-cyclopentane.

DETAILED DESCRIPTION OF THE INVENTION

In view of the above-described present status, the inventors have successfully completed the present invention by finding a novel compound with distinctive scent prepared by using camphor in a stationary condition in the price and resources as the starting compound as the consequence of extensive studies based on a conception that the tricyclic compounds would be synthesized with a considerable easiness when bicyclo-monoterpenes with a great availability are used in the synthesis.

That is, the present invention provides a derivative of bornane-3-spiro-1'-cyclopentane represented by the formula

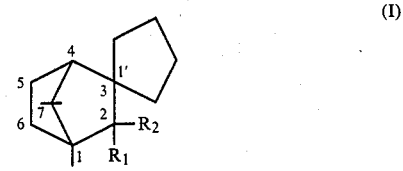

(I)

in which $R_1$ represents a hydrogen atom or a hydroxyl group, and $R_2$ represents a methoxyl group, an ethoxyl group, a formyloxyl group or an acetoxy group in the cases in which $R_1$ is a hydrogen atom or represents a methyl group or an ethyl group in the cases in which $R_1$ is a hydroxyl group, and the present invention also provides a perfumery composition containing the above compound.

The compound (I) of the invention is manufactured according to the following process using bornane-3-spiro-1'-cyclopentan-2-one (II) (hereinafter referred to as a ketone derivative) or bornane-3-spiro-1'-cyclopentan-2-ol (III) (hereinafter referred to an an alcoholic derivative) prepared from camphor by the method described for example in Japan Kokai Tokkyo Koho No. 62-16442.

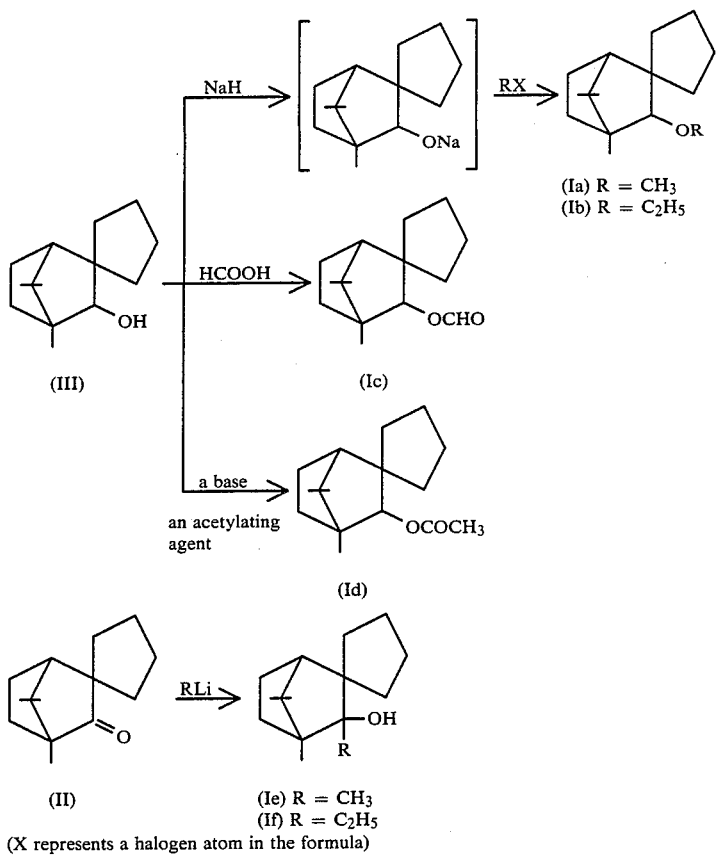

(Ia) R = CH₃
(Ib) R = C₂H₅

(X represents a halogen atom in the formula)

The compounds of the formula (I) in which $R_1$ represents a hydrogen atom are prepared by any of the following methods including: a method of obtaining ether derivatives (Ia) or (Ib) by the ether synthesis of Williamson in which an alkoxide obtained from an alcoholic derivative (III) by a treatment with sodium hydride is reacted with a halide such as methyl iodide, ethyl iodide and the like; a method of obtaining a formate ester (Ic) by the reaction of an alcoholic derivative (III) with an excessive amount of formic acid at room temperature; and a method of obtaining an acetic ester (Id) by the reaction of an alcoholic derivative (III) with an acetylating agent in the presence of a base.

Also, the compounds of the formula (I) in which $R_1$ represents a hydroxyl group are prepared by the method of obtaining (Ie) or (If) by the reaction of a ketone derivative (II) with a lithium reagent carried out in accordance with the method described in the book "Shin Jikken Kagaku Koza (New Lecture Courses of Experimental Chemistry), Vol. 14", pages 515 to 520.

The compound of formula (I) is obtained as a mixture of two distinctive species—different in the steric configuration of the substituting groups in the position 3 when prepared by way of one of the procedures of the above.

The compounds (I) of the invention emit distinctive scent different from that of the ketone derivatives (II) or the alcoholic derivatives (III) by the introduction of the group $R_2$ with simultaneous decrease of volatility and improvement in lingering of fragrance. That is, the compounds of (Ia) and (Ib) hardly emit amber-like odor characteristic in the alcoholic derivatives (III) giving grassy, metallic, moldy, woody or faintly resinous note scent by the compounds (Ia) or slightly woody, herbal or ether-like note scent by the compounds (Ib). The compounds (Ic) and (Id) do not emit fragrance of cedarwood note characteristic in the alcoholic derivatives (III) altogether giving amber-grease note or woody note scent by the compounds (Ic) or sweetishly woody, camphoraceous or faintly flower-like note scent by the compounds (Id). Furthermore, the compounds (Ie) and (If) do not emit camphoraceous note characteristic in the ketone derivatives (II) giving earthy, metallic, woody note or patchouli alcohol-like scent by the compounds (Ie) or slightly woody, amber-like or faintly earthy note scent by the compounds (If).

As mentioned in the above, each of the compounds of the invention emits a characteristic odor based on the woody note scent so that they can be widely used in the products which require perfuming such as high class perfumery compositions, liquid perfumes, soap, shampoo, hair rinse, detergents, cosmetics, atomizable spray agents, aromatics and the like as used alone or as a basic material for formulation of various perfumeries.

The invention is further explained referring to the examples in the following.

EXAMPLE 1

Synthesis of spiro[2-methoxybornane-3,1'-cyclopentane] (Ia)

A solution consisting of 1.2 g (0.03 moles) of sodium hydride and 10 ml of xylene is added dropwise with a solution consisting of 5 g (0.024 moles) of spiro[bornane-3,1'-cyclopentan-2-ol] and 5 ml of xylene at 100° C. while being stirred until the cease of hydrogen gas evolution. Thereafter, a mixture solution consisting of 5 g (0.035 moles) of methyl iodide and 5 ml of xylene is added to the solution being stirred dropwise within 15 minutes followed by continual stirring for 3 hours while the solution is kept at 100° C. After being cooled to room temperature, the solution is subjected to phase separation with added water and furthermore to washing 3 times with water. A purified product is obtained by fractional distillation under a reduced pressure following to removal of the solvent by distillation.

amount of the product: 5 g (yield 93.7%)

IR (liquid thin layer, cm$^{-1}$): 1120 ($\gamma_{C-O}$)

$^1$H-NMR (CDCl$_3$ solvent, TMS internal standard, δ ppm): 3.30 (singlet, —OC$\underline{H}_3$),

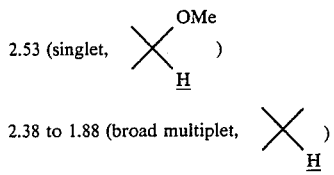

1.85 to 1.20 (complicated multiplet, —C$\underline{H}_2$—, 12H), 1.01 (singlet, C$\underline{H}_3$), 0.85 (singlet, C/e,uns/$\underline{H}$/ $_3$), 0.79 (singlet, C$\underline{H}_3$).

MS [m/e (relative intensity)]: 222(M$^+$, 22), 177(67), 113(34), 112(100), 108(35), 95(53), 85(83), 81(28), 55(28), 41(33).

Elementary analysis: Found C; 81.19%, H; 11.83%. Calculated C; 81.02%, H; 11.78%.

EXAMPLE 2

Synthesis of spiro[2-ethoxybornane-3,1'-cyclopentane] (Ib)

A solution consisting of 1.2 g (0.03 moles) of sodium hydride and 10 ml of xylene is added dropwise with a solution consisting of 5 g (0.024 moles) of spiro[bornane-3,1'-cyclopentan-2—ol] and 5 ml of xylene at 100° C. while being stirred until the cease of hydrogen gas evolution. Thereafter, the above reaction mixture is added with a solution consisting of 5 g (0.032 moles) of ehtyl iodide and 5 ml of xylene while being stirred at 100° C. within 15 minutes followed by being kept at the same temperature for 3 hours with continued stirring. After being cooled to room temperature, the solution is subjected to phase separation with added water and furthermore to washing 3 times with water. A purified product is obtained by fractional distillation under a reduced pressure following to removal of the solvent by distillation.

amount of the product: 5.1 g (yield 89.9%)

IR (liquid thin layer, cm$^{-1}$): 1120 ($\nu_{C-O}$)

$^1$H—NMR (CDCl$_3$ solvent, TMS internal standard, δ ppm):

3.40 (quartet, J=7.0 Hz, —OC$\underline{H}_2$—)

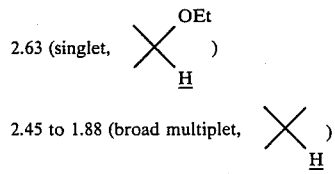

1.85 to 1.24 (complicated multiplet, —C$\underline{H}_2$—, 12H), 1.12 (triplet, J=7.2 Hz, —OCH$_2$—C$\underline{H}_3$), 1.03 (singlet, C$\underline{H}_3$), 0.83 (singlet, C$\underline{H}_3$), 0.78 (singlet, C$\underline{H}_3$).

MS [m/e (relative intensity)]: 236(M$^+$, 23), 177(77), 153(35), 127(41), 126(72), 108(46), 99(100), 95(53), 71(40), 41(44).

Elementary analysis: Found C; 81.35%, H; 12.10%. Calculated C; 81.29%, H; 11.94%.

EXAMPLE 3

Synthesis of spiro[2-formyloxybornane-3,1'-cyclopentane] (Ic)

A solution consisting of 20 g (0.087 moles) of spiro[bornane-3,1'-cyclopentan-2—ol] and 200 ml of formic acid is stirred for 3 hours while being chilled using ice water. The solution is subjected to phase separation with added ethyl ether and water followed by successive washing treatments of the organic phase using a saturated aqueous solution of sodium hydrogen carbonate and water in this order. After desiccation of the organic phase using anhydrous magnesium sulfate, the solid matter is separated by filtration and the filtrate is subjected to distillation under a reduced pressure for removal of the solvent. The residue is purified by column chromatography (the developing solvent: n-hexane/ethyl acetate=30/1) and a purified product is obtained after removal of the solvent by distillation.

amount of the product: 9 g (yield 43.8%)

IR (liquid thin layer, cm$^{-1}$): 1730 ($\nu_{C=O}$), 1160, 1180 ($\nu_{C-O}$)

$^1$H—NMR (CDCl$_3$ solvent, TMS internal standard, δ ppm):

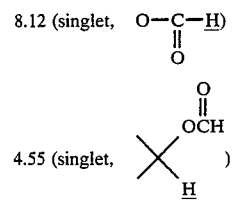

2.18 to 1.22 (complicated multiplet, (—C$\underline{H}_2$—, 12H)(—C$\underline{H}$<, 1H)), 1.08 (singlet, C$\underline{H}_3$), 0.82 (singlet, C$\underline{H}_3$), 0.78 (singlet, C$\underline{H}_3$).

MS [m/e (relative intensity)]: 236(M$^+$, 1), 110(31), 147(35), 41(59), 95(100).

Elemenary analysis: Found C; 75.95%, H; 10.42%. Calculated C; 76.23%, H; 10.23%.

EXAMPLE 4

Synthesis of spiro[2-acetoxybornane-3,1'-cyclopentane] (Id)

A solution consisting of 5 g (0.024 moles) of spiro[bornane-3,1'-cyclopentan-2—ol], 5 g of acetic anhydride and 5 ml of pyridine is stirred for 3 hours at room temperature. The solution is subjected to phase separation with added ethyl ether and water followed by successive washing treatments of the organic phase using 1N hydrchloric acid, a saturated aqueous solution of sodium hydrogen carbonate and water in this order. After desiccation of the organic phase using anhydrous magnesium sulfate, the solid matter is separated by filtration and a purified product is obtained from the filtrate subjected to removal of the solvent by distillation under a reduced pressure.

amount of the product: 6 g (yield 95.4%)

IR (liquid thin layer, cm$^{-1}$): 1745 ($\nu_{C=O}$), 1242 ($\nu_{C-O}$).

$^1$H—NMR (CDCl$_3$ solvent, TMS internal standard, δ ppm):

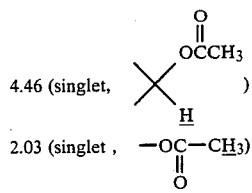

4.46 (singlet, H)

2.03 (singlet, —OC—CH$_3$ ‖ O)

1.90 to 1.20 (complicated multiplet, 13H)
1.08 (singlet, CH$_3$)
0.80 (singlet, CH$_3$)
0.75 (singlet, CH$_3$)

MS [m/e relative intensity)]: 250(M+, 1), 190(50), 175(37), 147(47), 140(38), 108(62), 98(100), 95(62), 43(80), 41(43).

Elementary analysis: Found C; 77.01%, H; 10.23%. Calculated C; 76.75%, H; 10.47%.

EXAMPLE 5

Synthesis of spiro[2-methylbornane-3,1'-cyclopentan-2—ol] Ie)

A solution consisting of 10 g (0.048 moles) of spiro[bornane-3,1'-cyclopentan-2-one] and 10 ml of desiccated ethyl ether is refrigerated to −78° C. under an inert gas atmosphere. The solution is added with 39 ml (0.062 moles) of methyl lithium (1.6 molar solution in ethyl ether) dropwise with stirring within 1 hour while being kept at the same temperature followed by temperature elevation back to room temperature. After continual stirring for 3 hours at room temperature, the solution is subjected to phase separation with added ethyl ether and water followed by successive washing treatments of the organic phase using a saturated aqueous solution of sodium hydrogen carbonate and then water with subsequent desiccation with anhydrous magnesium sulfate. By removal of the solvent by distillation, 10.4 g of a viscous liquid is obtained. A pure product is obtained from the liquid purified by column chromatography [the developing solvent: n-hexane (containing 3% of ethyl acetate] with subsequent removal of the solvent by distillation under a reduced pressure.

amount of the product: 8 g (yield 74.2%)

IR (liquid thin layer, cm$^{-1}$): 3450 to 3690 ($\nu_{O-H}$)

$^1$H—NMR (CDCl$_3$ solvent, TMS internal standard, δ ppm): 2.3 (triplet, J=7.0 Hz, <CH—) 1.79 to 1.27 (complicated multiplet, 12H)

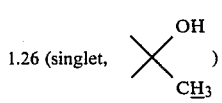

1.26 (singlet, OH, CH$_3$)

1.17 (singlet, CH$_3$),
0.86 (singlet, CH$_3$),
0.82 (singlet, CH$_3$),
MS [m/e (relative intensity)]:
222(M+, 1), 112(100), 95(49), 43(100), 41(92)

Elementary analysis: Found C; 81.15%, H; 11.53%. Calculated C; 81.02%, H; 11.78%.

EXAMPLE 6

Synthesis of spiro[2-ethylbornane-3,1'-cyclopentan-2—ol] (If)

A solution consisting of 1.3 g (0.056 moles) of lithium (30%, a mixture with liquid paraffin) and 10 ml of desiccated ethyl ether is added with a solution consisting of 4.4 g (0.028 moles) of ethyl iodide, 5.0 g (0.024 moles) of spiro[2-bornane-3,1'-cyclopentan-2-one] and 20 ml of desiccated ethyl ether dropwise within 30 minutes. After being stirred for 30 minutes at room temperature, the solution is added with ice-chilled water, extracted with ethyl ether, washed successively with 10% sulfuric acid and water, desiccated with anhydrous magnesium sulfate and subjected to removal of the solvent by distillation thus to give 5.2 g of a viscous liquid. A pure product is obtained from the liquid purified by column chromatography (the developing solvent: n-hexane/ethyl acetate=25/1) with subsequent removal of the solvent by distillation under a reduced pressure.

amount of the product: 4 g (yield 69.8%)

IR (liquid thin layer, cm$^{-1}$):
3450 to 3650 (broad absorption peak, $\nu_{O-H}$)

$^1$H—NMR (CDCl$_3$ solvent, TMS internal standard, δ ppm): 0.53 to 0.96 (complicated multiplet, CH$_3$, 9H)
1.07 (singlet, CH$_3$)

1.13 to 2.23 (complicated multiplet, —CH$_2$—, 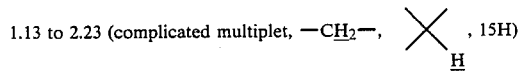, 15H)

MS [m/e (relative intensity)]:
236(M+, 2), 126(100), 123(32), 109(36), 99(51), 97(60), 95(59), 69(43), 57(52), 41(36)

Elementary analysis: Found C; 80.15%, H; 12.05%. Calculated C; 81.29%, H; 11.94%.

EXAMPLE 7

| forest note perfumery compositions | parts by weight |
|---|---|
| lemon oil | 50 |
| bergamot base | 80 |
| pine needle base | 113 |
| aldehyde C-12MNA | 2 |
| isobornyl acetate | 50 |
| p-t-butyl cyclohexyl acetate | 50 |
| acetyl cedrene | 30 |
| far balsam absolute | 5 |
| treemoss absolute 50% DEP[1] | 20 |
| citronellol | 50 |
| geranyol | 100 |
| hexyl cinnamic aldehyde | 120 |
| methyl dihydro jasmonate | 50 |
| Lyral[2] | 30 |
| Galaxolide 50 DEP[3] | 150 |
| total | 900 |

[1]50% DEP: 50% solution in diethyl phthalate
[2]Lyral: a trade name for IFF Company 4-(4-hydroxy-4-methylpentyl)-3-cyclohexene-1-carboxyaldehyde
[3]Glaxolide 50 DEP: a trade name for IFF Company 1,3,4,6,7,8-hexahydro-4,6,6,7,8,8-hexamethyl-cyclopenta-γ-2-benzopyran By compounding 100 parts by weight of the compound (Ic) of the present invention with 900 parts by weight of the above perfume, a forest note perfumery composition rich in woody and amber notes and with a feeling of abundance was obtained.

EXAMPLE 8

| perfumes for cologne for men | parts by weight |
|---|---|
| bergamot oil Italy BGF[1] | 50 |

| perfumes for cologne for men | parts by weight |
|---|---|
| lemon oil Sunkist BGF | 30 |
| pine oil China | 20 |
| aromoase oil | 10 |
| basil oil | 5 |
| lavender oil | 15 |
| 2,4-dimethyl-3-cyclohexene-1-carboxyaldehyde | 5 |
| jasmine base | 40 |
| patchouli oil | 10 |
| acetyl cedrene | 200 |
| oakmoss absolute 50% DEP[2] | 30 |
| Galaxolide 50 DEP[3] | 80 |
| amber base | 20 |
| thyme oil red | 5 |
| eugenol | 20 |
| dipropyleneglycol | 260 |
| total | 800 |

[1]BGF: bergaptene-free grade
[2]50% DEP: 50% solution in diethyl phthalate
[3]Galaxolide 50 DEP: a trade name for IFF company 1,3,4,6,7,8-hexahydro-4,6,6,7,8,8-hexamethyl-cyclopenta-γ—2-benzopyran By compounding 200 parts by weight of the compound (Ie) of the present invention with 800 parts by weight of the above perfume, a perfumery for cologne for men with increased woody note rich in aromatic feeling was obtained.

We claim:

1. A derivative of bornane-3-spiro-1'cyclopentane represented by the general formula

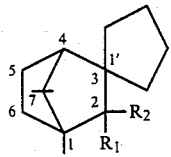

(I)

in which $R_1$ represents a hydrogen atom or a hydroxyl group and $R_2$ represents a methoxyl group, an ethoxyl group, a formuloxyl group or an acetoxyl group in the cases in which said $R_1$ is a hydrogen atom or represents a methyl group or an ethyl group in the cases in which said $R_1$ is a hydroxyl group.

2. The derivative of bornane-3-spiro-1'-cyclopentane according to claim 1, wherein said $R_1$ is a hydrogen atom and said $R_2$ is a methoxyl group being spiro[2-methoxybornane-3,1'-cyclopentane].

3. The derivative of bornane-3-spiro-1'-cyclopentane according to claim 1, wherein said $R_1$ is a hydrogen atom and said $R_2$ is an ethoxyl group being spiro[2-ethoxybornane-3,1'-cyclopentane].

4. The derivative of bornane-3-spiro-1'-cyclopentane according to claim 1, wherein said $R_1$ is a hydrogen atom and said $R_2$ is a formyloxyl group being spiro[2-formyloxybornane-3,1'-cyclopentane].

5. The derivative of bornane-3-spiro-1'-cyclopentane according to claim 1, wherein said $R_1$ is a hydrogen atom and said $R_2$ is an acetoxyl group being spiro[2-acetoxybornane-3,1'-cyclopentane].

6. The derivative of bornane-3-spiro-1'-cyclopentane according to claim 1, wherein said $R_1$ is a hydroxyl group and said $R_2$ is a methyl group being spiro[2-methylbornane-3,1'-cyclopentan-2—ol].

7. The derivative of bornane-3-spiro-1'-cyclopentane according to claim 1, wherein said $R_1$ is a hydroxyl group and said $R_2$ is an ethyl group being spiro[2-ethylbornane-3,1'-cyclopentan-2—ol].

8. A perfumery composition comprising a derivative of bornane-3-spiro-1'-cyclopentane represented by the general formula

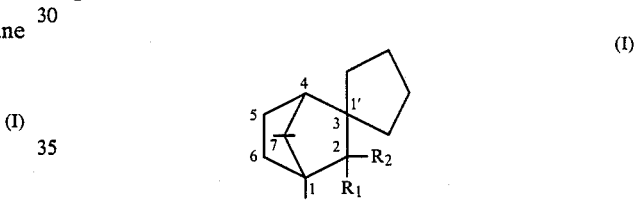

(I)

in which $R_1$ represents a hydrogen atom or a hydroxyl group and $R_2$ represents a methoxyl group, an ethoxyl group, a formyloxyl group or an acetoxyl group in the cases in which said $R_1$ is a hydrogen atom or represents a methyl group or an ethyl group in the cases in which said $R_1$ is a hydroxy group.

* * * * *